United States Patent
Culp

(10) Patent No.: US 7,790,073 B2
(45) Date of Patent: Sep. 7, 2010

(54) DENTAL COMPOSITES AND PLACEMENT TECHNIQUES FOR DIRECT RESTORATIONS

(75) Inventor: Terry Lee Culp, Bradenton, FL (US)

(73) Assignee: Ivoclar Vivadent Inc., Amherst, NY (US)

(*) Notice: Subject to any disclaimer, the term of this patent is extended or adjusted under 35 U.S.C. 154(b) by 0 days.

(21) Appl. No.: 12/138,202

(22) Filed: Jun. 12, 2008

(65) Prior Publication Data

US 2008/0245268 A1 Oct. 9, 2008

Related U.S. Application Data

(63) Continuation of application No. 10/824,799, filed on Apr. 15, 2004, now abandoned.

(60) Provisional application No. 60/531,886, filed on Dec. 22, 2003.

(51) Int. Cl.
*A61C 13/00* (2006.01)
*A61C 19/10* (2006.01)
*A61C 13/08* (2006.01)

(52) U.S. Cl. .................. 264/20; 264/19; 427/2.29; 106/35; 433/26; 433/203.1; 433/212.1

(58) Field of Classification Search .................. None
See application file for complete search history.

(56) References Cited

U.S. PATENT DOCUMENTS

| | | |
|---|---|---|
| 3,066,112 A | 11/1962 | Bowen |
| 3,179,623 A | 4/1965 | Bowen |
| 3,405,446 A | 10/1968 | Wiener |
| 3,452,437 A | 7/1969 | Chang |
| 3,471,596 A | 10/1969 | Petner et al. |
| 4,141,144 A | 2/1979 | Lustgarten |
| 4,189,325 A | 2/1980 | Barrett et al. |
| 4,221,698 A | 9/1980 | Lee, Jr. et al. |
| 4,224,023 A | 9/1980 | Cheung |
| 4,379,695 A | 4/1983 | Orlowski et al. |
| 4,381,918 A | 5/1983 | Ehrnford |
| 4,392,828 A | 7/1983 | Ehrnford |
| 4,481,227 A | 11/1984 | Tanaka |
| 4,648,843 A | 3/1987 | Mitra |
| 4,674,980 A | 6/1987 | Ibsen et al. |
| 4,741,699 A | 5/1988 | Kosmos |
| 4,744,759 A | 5/1988 | Bowen |
| 4,802,850 A * | 2/1989 | Boon .................. 433/26 |
| 4,828,117 A | 5/1989 | Panzera et al. |
| 4,874,315 A | 10/1989 | Featherstone et al. |
| 4,952,530 A | 8/1990 | Brosnan et al. |
| 5,089,306 A | 2/1992 | Grossman et al. |
| 5,125,970 A | 6/1992 | Klepacki |
| 5,127,834 A | 7/1992 | Hasegawa et al. |
| 5,127,835 A | 7/1992 | Yamaguchi et al. |
| 5,162,130 A | 11/1992 | McLaughlin |
| 5,192,207 A | 3/1993 | Rosellini |
| 5,348,475 A * | 9/1994 | Waknine et al. .......... 433/215 |
| 5,430,074 A | 7/1995 | Barnes et al. |
| 5,482,464 A | 1/1996 | Shimosawa et al. |
| 5,558,701 A | 9/1996 | Patel |
| 5,621,035 A | 4/1997 | Lyles et al. |
| 5,624,262 A | 4/1997 | Yarovesky et al. |
| 5,685,717 A | 11/1997 | Kramer |
| 5,762,502 A | 6/1998 | Bahn et al. |
| 5,775,912 A | 7/1998 | Panzera et al. |
| 5,844,018 A | 12/1998 | Jacobs et al. |
| 5,906,490 A | 5/1999 | Kramer Primus et al. |
| 5,997,302 A | 12/1999 | Alpert |
| 6,007,332 A | 12/1999 | O'Brien |
| 6,008,264 A | 12/1999 | Ostler et al. |
| 6,013,694 A | 1/2000 | Jia et al. |
| 6,030,209 A | 2/2000 | Panzera et al. |
| 6,033,222 A | 3/2000 | Schneider, II et al. |
| 6,206,958 B1 | 3/2001 | Panzera et al. |
| 6,262,142 B1 | 7/2001 | Wang et al. |
| 6,300,390 B1 | 10/2001 | Angeletakis |
| 6,315,554 B1 | 11/2001 | Coste et al. |
| 6,315,567 B1 | 11/2001 | Hasel |
| 6,384,106 B1 | 5/2002 | Angeletakis |
| 7,086,863 B2 | 8/2006 | Van der Zel |
| 2002/0064750 A1 | 5/2002 | Morris et al. |
| 2002/0081547 A1 | 6/2002 | Kerschbaumer et al. |
| 2003/0124481 A1 | 7/2003 | Zun |
| 2003/0152891 A1 | 8/2003 | Chiu et al. |
| 2003/0175660 A1 | 9/2003 | Yin et al. |
| 2003/0180687 A1 | 9/2003 | Mrotzek et al. |

OTHER PUBLICATIONS

Bilmeyer, F.W., Principles of Color Technology, $2^{nd}$ ed., John Wiley, 1981 (Table of Contents only).

* cited by examiner

*Primary Examiner*—Jeffrey Wollschlager

(57) ABSTRACT

Colorless dental compositions for restoring the enamel layer of a tooth are disclosed. The colorless enamel compositions are combined with pigmented dentin compositions to provide a true color match and natural esthetics. Methods that utilize the compositions in placement/build-up techniques in direct restorations are also disclosed.

11 Claims, 5 Drawing Sheets

DENTAL COMPOSITES AND PLACEMENT TECHNIQUES FOR DIRECT RESTORATIONS

This application is a continuation of U.S. patent application Ser. No. 10/824,799, filed Apr. 15, 2004, which claims the benefit of U.S. Provisional Patent Application Ser. No. 60/531,886, filed Dec. 22, 2003, each of which is hereby incorporated by reference in its entirety.

FIELD OF THE INVENTION

This invention relates to dental composites and methods for their use in placement/build-up techniques in direct restorations.

BACKGROUND OF THE INVENTION

Dental restoratives are well known in the art and include for example, crowns, inlays, onlays, veneers, and fillings. Restorative materials are those utilized in repairing a damaged tooth, or in replacing an entire tooth. When repairing a damaged tooth, it is desirable not only that the tooth be returned to a useful state, but that it also be returned as close as possible to its natural aesthetic state, such that the color and appearance of the restored tooth blend in with the surrounding natural dentition.

Dental restorations are typically prepared according to two different techniques: (1) in situ or direct restorations, wherein the restoration is fabricated directly in the patient's mouth; and (2) indirect restorations, wherein the restoration is fabricated directly in a dental laboratory and subsequently communicated to the dental practitioner for placement in the patient's mouth. Direct restorations typically involve issues such as repairing a cracked tooth, treating a tooth for decay or filling in a space between adjoining teeth. Indirect restoration techniques are typically employed for more complex dental repairs, such as, for example, the replacement of a complete tooth. Indirect restorations are typically fabricated from ceramics or porcelains and involve the build-up of sequential layers of material. While indirect techniques are inherently more expensive, time consuming and require a greater level of technical expertise than direct placement techniques, they allow for a higher degree of aesthetic precision and typically provide a very natural looking restoration.

In a typical direct restoration, the tooth to be restored is initially treated by removing the decayed or damaged material and then the removed portion is restored with a dental restorative material. Conventional restorative materials include dental amalgams or metal alloys; flowable dental composites, such as those described in U.S. Pat. Nos. 3,066,112; 3,179,623; and 4,744,759 to Bowen; and condensable dental composites, such as those described in U.S. Pat. Nos. 4,381,918 and 4,392,828 to Ehrnford; U.S. Pat. No. 4,952,530 to Brosnan et al; U.S. Pat. No. 5,621,035 to Lyles et al.; and U.S. Pat. No. 6,013,694 to Jia et al. U.S. Pat. No. 6,300,390 to Angeletakis describes resin-based dental restoratives incorporating uniformly dispersed submicron sized reinforcing particulates and published United States Patent Application No. 2003/0175660 to Yin et al, describes a restorative composite including a spherical or sub-micron size filler bound together by a polyurethane dimethacrylate ester oligomer.

Dental restorative composites are typically dispersions of micro sized glass filler particles in a methacrylate-type monomer resin. Splintered, pre-polymerized particles or ground suspensions of silica in pre-polymerized dental resins, may also be used. Additives such as pigments, initiators and stabilizers may be included in these types of composites. Flowable dental composites are typically a reinforcing particulate inorganic filler bound together by a polymeric matrix. One commonly used flowable dental composite is a mixture of an organic polymer known as bisphenol-A-glycidyl methacrylate (Bis-GMA) and inorganic particles such as quartz, borosilicate glass, and lithium aluminum silicate. Typical condensable dental composites include various other alternative inorganic filler materials in a polymer matrix.

Due to their metallic appearance and low adherence to natural tooth structure, the growth of amalgams in dental restorations has remained flat with increasing growth in current dental practices typically utilizing various light-curable dental composites for fabricating restorations. In addition to being durable and wear resistant, dental composites are readily adaptable to coloring and can therefore provide a more natural looking restoration.

Conventional composite placement techniques for direct restorations typically include the steps of:
 cleaning the tooth and while moistened, evaluating the overall shade/color appearance;
 preparing the area for restoration, i.e., removing decayed/damaged enamel and dentin;
 applying a bonding agent to the prepared area;
 selecting correspondingly-colored dentin and enamel restorative materials, respectively;
 applying the colored dentin material to restore the dentin layer;
 applying the colored enamel material to restore the enamel layer; and
 finishing and polishing the restoration.

Optional steps might include applying a flowable composite prior to applying the colored dentin material, in order to fill in any voids or irregularities that may exist in the floor of the restoration area, or applying special effects to the restoration prior to finishing and polishing.

One of the most exacting and time consuming aspects of dental restorations, whether involving direct or indirect placement techniques, is that of properly matching the color of the restoration to that of the original tooth. In the context of clinical dentistry, the term "color" involves three discrete concepts: hue, chroma and value. Hue is the dimension of color that enables us to distinguish one family of color from another; chroma defines the relative intensity of a particular color, i.e., the more intense a color is, the higher its chroma level; and value describes the relative whiteness or blackness of a particular color, i.e., the brighter the color, the higher its value. In addition to these concepts, characteristics such as opacity, fluorescence, and translucency may also be considered during a dental restoration.

To aid in the determination of tooth color, a dental practitioner will often utilize a dental shade guide or other such similar device, to evaluate the color characteristics of the tooth. A typical dental shade guide has a base supporting a plurality of tabs or other indicia, each of which corresponds to a different color. A given guide may include a number of sets of tabs, one representing standard tooth colors, one representing standard dentin colors and one representing standard enamel colors. The colors are typically defined according to the CIE L*a*b* system wherein "L" refers to value (black is 0 and white is 100), "a" is a measurement on the red to green scale, and "b" is a measurement on the blue to yellow scale (Bilmeyer, F. W., *Principles of Color Technology*, $2^{nd}$ ed., John Wiley, 1981).

Conventional shade guides are disclosed, for example, in U.S. Pat. No. 6,315,554 to Coste et al. and U.S. Pat. No. 6,030,209 to Panzera et al and published United States Patent Application Nos. 2003/0124481 to Zun; 2002/0081547 to Kerschbaumer et al.; and 2002/0064750 to Morris et al. Commercially available shade guides include Vitapan Classical™ (formerly, Vita-Lumin™ Vacuum Shade Guide), Vitapan 3-D Master™ (Vident, Brea, Calif.), Bioform™ and TruMatch™ (Dentsply International, Inc., Milford, Del.)

Conventional restoration techniques utilize a philosophy that both the dentin and enamel layers of teeth possess a color or shade which influences the overall color and appearance of the tooth. Standard shade guides categorize these colors into four basic groups: A, B, C, and D. In addition, each group may itself be internally categorized to include shades that add further characterization to restorations. Darker shades, for example, have been developed for older patients and bleach shades have been introduced in response to an increased use of whitening agents. In practice, the practitioner first chooses the color tab that most closely matches the overall color of the damaged tooth. The correspondingly-colored dentin and enamel restorative materials are then prepared and placed on the tooth. Thus, the color of the finished restoration will result from a combination of the colors of the dentin and the enamel restorative materials.

One drawback of this technique is therefore, the high level of skill and effort required to assure that the colored dentin and enamel materials, when combined, create the appropriate color result so that the restoration blends in with the surrounding dentition. As a result, although conventional tooth-colored composite placement techniques provide restorations that are much more aesthetically appealing than had previously been achieved with amalgams, for example, improved techniques continue to be sought. Direct placement techniques that provide a restoration having the aesthetic properties of an indirect ceramic restoration would be highly desirable. The principles of the present invention provide such techniques.

SUMMARY OF THE INVENTION

In accordance with the principals of the present invention, a direct restoration having the aesthetic qualities of an indirectly fabricated ceramic restoration is provided. In one embodiment, a method is provided for fabricating a direct dental restoration having the color of a natural tooth, including:

matching the value shade of the tooth to be restored to a colorless enamel value restorative material;
preparing the tooth for restoration;
matching the shade of a dentin layer of the tooth to a shaded dentin restorative material;
applying the matched dentin restorative material to the tooth to be restored; and
applying, over the dentin restorative material, the matched colorless enamel value restorative material to the tooth to be restored.

In a further embodiment there is provided a method for fabricating a direct dental restoration having the color of a natural tooth, including:

cleaning the tooth and while moistened, matching the value shade of the tooth to be restored to a colorless enamel value restorative material;
preparing the tooth for restoration by removing decayed/damaged enamel and dentin or reshaping the tooth for cosmetic restoration;
matching the shade of a dentin layer of the tooth to a shaded dentin restorative material;
applying a bonding agent to the prepared area;
applying a flowable composite prior to applying the colored dentin material, in order to fill in any voids or irregularities that may exist in the floor of the restoration area;
applying the matched dentin restorative material to the tooth to be restored;
applying, over the dentin restorative material, the matched colorless enamel value restorative material to the tooth to be restored;
applying special effects, including internal characterization materials including white or blue shaded or staining or tinting materials to the restoration prior to the final restorative layer;
applying an external characterization material including a translucent material to the external surface of the restoration;
finishing by shaping or contouring the restoration; and
polishing the restoration.

In a further embodiment there is provided an enamel restorative material colorless to the naked eye, having no added pigment and a low value shade; a medium value shade; or a high value shade.

In another embodiment there is provided a cured dental composite restoration including a highly chromatic shaded dentin restorative material and an enamel restorative material colorless to the naked eye, having no added pigment and a low value shade; a medium value shade; or a high value shade.

DETAILED DESCRIPTION OF THE INVENTION

Figure 1:
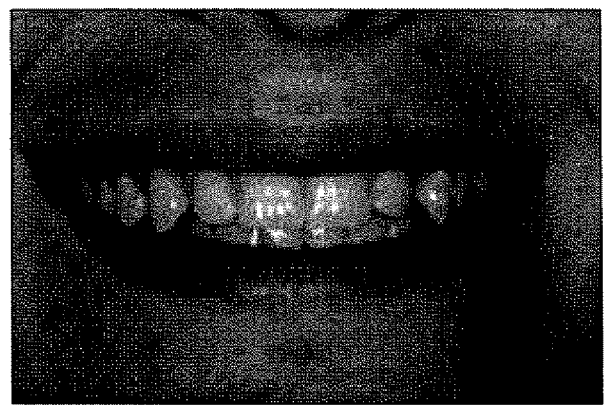
FIGS. 1 through 15 illustrate the clinical case study described in Example 2.

The direct restoration technique of the present invention utilizes the recognition that tooth enamel is a colorless material and that the "color" of a tooth resides in the dentin layer. It is the degree to which the color of the highly chromatic dentin material shines through the colorless enamel that determines a tooth's color. In light of this recognition, conventional direct restoration techniques which require a color determination for both the dentin and enamel layers can be simplified in providing natural-appearing and aesthetic restorations.

The present invention utilizes the concept that the color of a natural tooth is determined by the color of the dentin layer and that the enamel layer is colorless, yet having a value shade. Value shade is the parameter of color that describes its relative brightness or darkness, the higher the value, the brighter the color. The present invention eliminates the need to select colored restorative dentin materials and colored restorative enamel materials that when combined match the ultimate color of the final restoration. Rather, the practitioner is simply required to match the color of the dentin layer. The tooth is evaluated simply on its value, or level of brightness. The color of the restoration is therefore determined by the "color" of the chromatic dentin restorative material and the value of the "colorless" enamel restorative material. The enamel restorative material is therefore also appropriately referred to as the "value restorative". In accordance with the enamel restorative material of the present invention, "colorless" means that the material is colorless to the naked eye. Moreover, no pigment is added to the formulation of the enamel restorative material.

In accordance with the principles of the invention, a new enamel shade group referred to as value shades is provided.

The group includes colorless shades measured on a scale of black to white. The value shades contain no hue or chroma dimension that is detectible by the naked eye. Preferably, the group includes three shades, referenced as low value, medium value, and high value. The low value shade is the darkest (i.e., most closely approaching black), the high value shade is the brightest (i.e., most closely approaching white), and the medium value shade is generally in between, however, other groupings are possible. As the value shades contain no added pigment, they are inherently more translucent than conventional standard enamel shades.

The colorless enamel value shade restorative material typically includes a filler component, a polymer matrix/monomer component, and a polymerization catalyst, such as those known in the art. Suitable filler materials include, for example, finely divided solids such as silica, glass, zirconium, aluminum oxide, crystalline quartz, glass beads, or mixtures of glass beads and quartz. The polymeric matrix may be, for example, an acrylic or epoxy resin or other type of carbon-based polymer. Examples of polymeric materials (resins) suitable for use as dental composites are described in U.S. Pat. Nos. 3,066,112; 3,179,623; 4,744,759; and 5,997,302, the entire contents of which are incorporated herein by reference in their entirety.

Thus, in accordance with the method of the present invention, the dental practitioner is required to make a "color" match with respect to only the dentin layer of the tooth to be restored. The enamel layer is evaluated simply on the concept of value. As conventional direct placement techniques do not consider the concept of value alone, the present invention provides a more simplified method for fabricating a direct restoration with a natural looking and aesthetic result.

In accordance with the methods of the present invention, the area of the tooth to be restored is cleaned. Preferably, while the tooth is moist and hydrated, the tooth is evaluated with respect to its value shade, for example, it is matched to a value shade having low value, medium value, or high value. Preferably, the value shade is determined through the use of a shade guide that includes the colorless value shade indicia. The value shade guide may, for example, be adapted to include three value shade tabs, referenced as low value, medium value, and high value, wherein the closest match to the value shade of the tooth is determined by comparison with each of the three tabs.

The tooth is then prepped according to conventional preparation techniques to remove the decayed/damaged portions of the enamel and dentin. Methods for tooth preparation are well-known in the art and include for example, acid etching, cavo surface beveling, carbide friction-grip burs, "blasting" with an air abrasion unit, and "vaporization" with a dental laser. The tooth is then washed with water. While excess water is removed by blotting or by treating with a stream of air, the tooth surface is preferably left moist, as a dry surface can result in a poor bond between the tooth and the restorative materials. Tooth preparation may also include reshaping of the tooth for cosmetic restoration with or without removing damaged portions.

Following tooth preparation, the practitioner determines the color of the chromatic dentin layer of the tooth. This may be accomplished, for example, by matching with the aid of a conventional dentin shade guide or other similar procedure. The dentin is matched to a dental composite material for use in restoring the dentin layer which has been prepared and colored to correspond to the natural dentin, all according to conventional preparation and coloring techniques.

Following selection of the dentin shade, a thin layer of a bonding agent, such as a primer, an adhesive, or a primer/adhesive mixture, is typically applied. The bonding agent enhances the attachment of the restorative materials to the natural dentin and enamel. Such products and methods for their application are well-known in the art. Preferably, the bonding agent is applied in two consecutive coats, which are then treated with air to remove the solvent and cured, typically by exposure to a visible light source for about 10 seconds.

As in conventional direct restoration procedures, a thin (0.5 to 1.0 mm) layer of a flowable dental composite material may optionally be placed in the cavity and cured. This material is commonly used to ensure that all surfaces and voids within the cavity are wetted, in order to provide the best possible attachment surface for the restorative materials. Materials for use in this step, and methods for their placement, are well-known in the art. One such method is described in U.S. Pat. No. 6,315,567 to Hasel, the entire content of which is incorporated herein by reference.

The practitioner then utilizes techniques in accordance with the present invention to build-up the restoration by placing sequential layers of restorative materials within the area to be restored. The dentin-colored restorative material is used to restore the dentin layer and optionally a portion of the enamel layer and the colorless enamel-value shade restorative material is used to restore the enamel layer. Preferably, each of these restorative materials are place in increments of 2 mm and then polymerized or hardened. Polymerization is typically achieved with the use of a curing light, although other conventional methods may also be used. The restoration is completed with known polishing and finishing techniques.

Optional steps may include for example, the application of special effects shades, such as tinting or staining materials, just below the final restorative layer. Special effects may include, for example, a white or blue shade applied prior to the final colorless enamel-value shade restorative material, in the case where the natural tooth had previously undergone whitening. These special effects provide internal characterization. Frequently, practitioners will also apply a layer of a very translucent material to the external surface of the restoration to give a life-like aesthetic appearance. Typically, such translucent materials are categorized as amber, clear or super clear which provide surface or external characterization with translucency levels up to 50% or more.

EXAMPLES

Example 1

Below is a listing of the CIELAB color co-ordinates ($L^*$, $a^*$, $b^*$) as well as the degrees of opacity (CR) and translucency (T) of the high, medium, and low value shade enamel restoration materials of the present invention:

|  | $L^*$ | $a^*$ | $b^*$ | CR (%) | T(%) |
|---|---|---|---|---|---|
| Value High | 76 | −1.85 | 7.3 | 45 | 20.0 |
| Value Medium | 73 | −1.57 | 5.5 | 52 | 17.3 |
| Value Low | 63 | −0.6 | 5.8 | 47 | 23.2 |

Example 2

A 27-year-old female presented with the complaint that she did not like the spaces between her teeth (FIG. 1). Facially, the diastemas were not as apparent, but she was very aware of the spaces and wanted the problem corrected. She felt the appearance of her smile would improve if the diastemas were closed.

Figure 2:
Figure 3:

A clinical evaluation was completed and 35-mm photographs were taken. Diastemas between tooth Nos. 5 and 6, 6 and 7, and 10 and 11 were noted (FIGS. 2 and 3). She demonstrated no pathology and had good occlusal function. The patient was not dissatisfied with the color or the overall shape and contour of her dentition.

During the consultation, treatment options were reviewed and the decision was made to correct the diastemas using a direct composition system (4 Seasons® Direct Esthetic Composite System; Ivoclar Vivadent, Inc., Schaan, LI). A conservative approach was warranted, given the health of the surrounding dentition and the patient's overall satisfaction with the existing color and shape of her teeth. Therefore, the factors to be considered in this case included the following: ensuring that the restorations would match the surrounding dentition; achieving width-to-length ratios that would be acceptable to the patient; and achieving proper occlusal function. At the time of presentation, the width-to-length ratio was 56% to 70%; the ideal would be 80%.

The patient would benefit from a direct veneering technique for several reasons. Specifically, there would be only one appointment necessary to complete the restorations, there would be no temporization, and the result not only would be noninvasive but also reversible. The direct veneering technique would allow the dentist to utilize artistic skills to create additional tooth structure with the same qualities as the natural dentition.

The composite system of choice (4 Seasons® Direct Esthetic Composite System) was selected based on the number and accuracy of shades available. The material's "true color confidence" resulted from four years of clinical research and testing that produced a true match to standard A-D shades in addition to mimicking the transparency, opacity, fluorescence, and value of natural tooth structure. With forty composite shades and shade effects available, it would be possible in this case to match even the most aesthetically challenging aspects of this patient's dentition.

Figure 4:
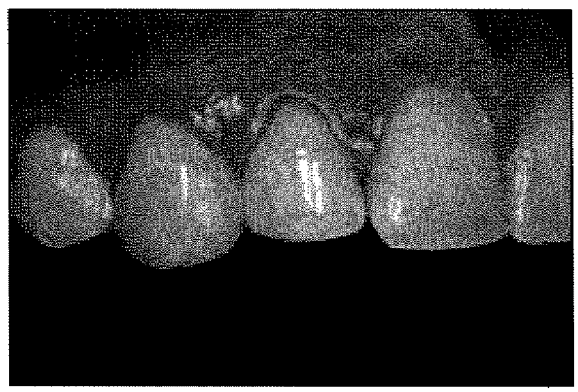
Figure 5:
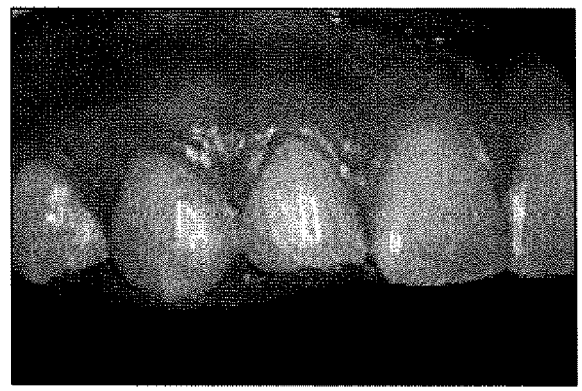
Figure 6:
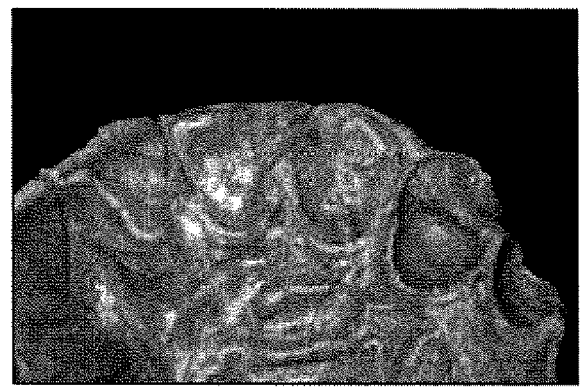

A shade guide (4 Seasons® Shade Guide; Ivoclar Vivadent, Inc., Schaan, LI) was used to determine which shade(s) of composite to place. The advantage of using this shade guide is that the shade tabs are made with ceramic to ensure long-term color stability and enable a consistent shade match. Once the shades were determined, the selected composite shades were placed on the unetched tooth surfaces of the mesial aspect of tooth No. 5, the mesial and distal aspects of tooth Nos. 6 and 10, and the distal aspect of tooth No. 7, then light-cured to simulate the permanent restorations (FIG. 4). This "mock-up" verified accurate shade selection and provided a basis for the creation of a putty matrix (Virtual Putty™; Ivoclar Vivadent, Inc., Schaan, LI), which would serve as a guide for proper lingual contouring and assist in determining the appropriate length of the permanent restorations (FIGS. 5 and 6).

Figure 7:
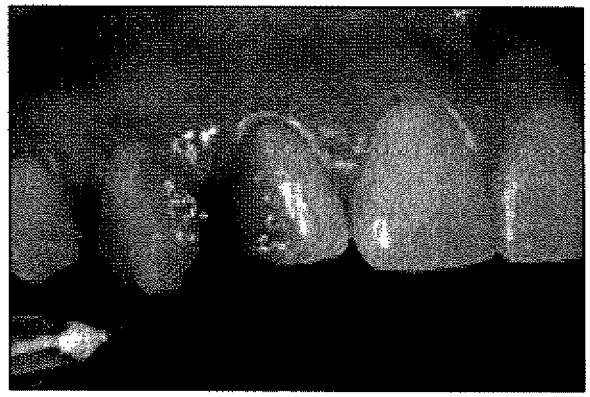
Figure 8:
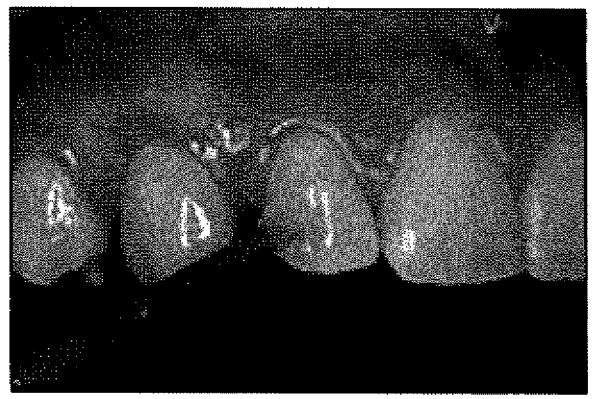

Once the putty matrix was complete, the interim composite material was removed with an explorer or curette and the teeth were then cleansed with pumice and isolated with cotton rolls. The teeth were acid-etched with 37% phosphoric acid for 30 seconds (FIG. 7), rinsed thoroughly, and dried. A light-cured, single-component bonding agent (Excite®; Ivoclar Vivadent, Inc., Schaan, LI) was applied to the etched surfaces and light-cured for 10 to 20 seconds (FIG. 8). Once a homogeneous gloss was apparent on all prepared areas, the surfaces were then ready for placement of the permanent restorations.

The restorations were placed according to an anatomical technique that involved the use of a highly chromatic dentin shade composite overlaid with a colorless enamel value composite. In addition to a full complement of enamel and dentin shades that correspond to the A-D shade range, the selected composite system also featured three unique value shades (high, medium, and low) that mimic natural enamel in the manner in which it diffuses the underlying dentin color to create a natural-looking depth and appearance.

Figure 9:

The lateral incisors were evaluated, and a dentin shade of A2 was selected. A thin coating of A2 dentin composite was placed on distal aspects of the lateral teeth, contoured with a brush and composite instrument (FIG. 9), then light-cured for 10 seconds with a turbo tip on an Astralis® 10 (Ivoclar Vivadent, Inc., Schaan, LI). The dentin shade was then overlaid with a medium-value shaded enamel composite, which was also light-cured for 20 seconds with a turbo tip on an Astralis® 10 since this was the final cure. An A3 dentin composite was then similarly placed on the mesial aspects of the canines and cured, after which it was overlaid with a medium-value shaded enamel composite and light-cured.

Figure 10:
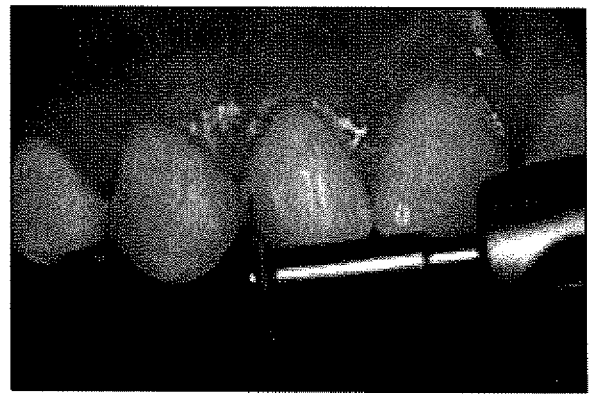
Figure 11:
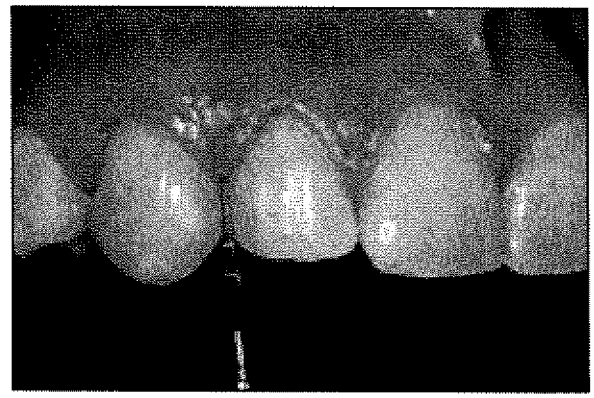
Figure 12:
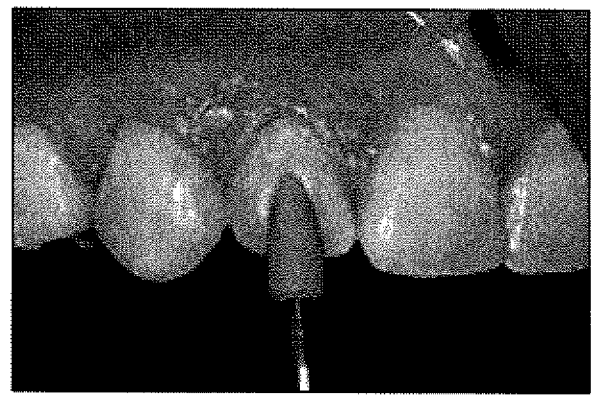
Figure 13:
Figure 14:
Figure 15:
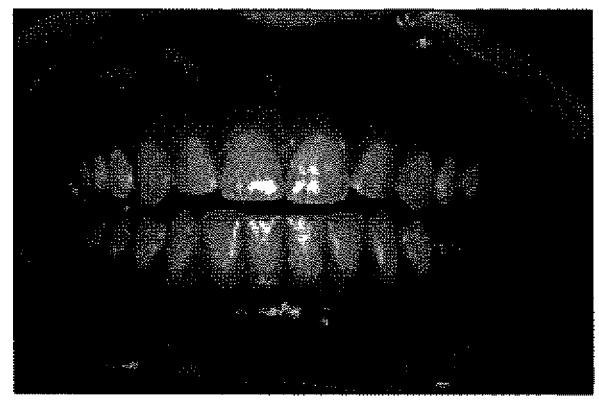

The restorations were shaped and contoured using medium, fine, and superfine discs (3M™ ESPE™ S f-Lex™ Xt; 3M ESPE AG, Seefeld, Germany) (FIG. 10), and the final contours were made with a finishing bur (Axis™ TDF9 Finishing Bur, Axis Dental, Irving, Tex.) (FIG. 11). To achieve a nice, polished surface a POGO™ Wheel (DENTSPLY Caulk, DENTSPLY International, Inc., York Pa.) and Astropol® points (Ivoclar Vivadent, Inc., Schaan, LI) were used (FIG. 12). The final restorations were photographed at completion (FIGS. 13 and 14) and again 5 days postoperatively (FIG. 15).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method for fabricating a direct dental restoration having the color of a natural tooth, comprising:
    matching the value shade of a natural tooth to be restored to an enamel value restorative material;
    preparing the tooth for restoration;
    matching the color shade of a dentin layer of the tooth to a shaded dentin restorative material;
    applying the matched dentin restorative material to the tooth to be restored; and
    applying, over the dentin restorative material, the matched enamel value restorative material to the tooth to be restored, wherein the color of the natural tooth is matched by the dental restoration by matching only the color shade of the dentin layer and the value shade of the enamel of the natural tooth.

2. The method of claim 1, wherein applying comprises placing a thin coating of restorative material on the tooth and polymerizing the restorative material.

3. The method of claim 2, wherein the restorative material is polymerized by light-curing.

4. The method of claim 1, wherein preparing the tooth for restoration comprises removing a portion of the enamel layer and a portion of a dentin layer of the tooth.

5. The method of claim 1, wherein preparing the tooth for restoration comprises reshaping the tooth for a cosmetic restoration.

6. The method of claim 1, further comprising applying a bonding agent to the exposed dentin and enamel when preparing the tooth for restoration to enhance the bonding of the composite restorative material.

7. The method of claim 1, further comprising finishing and polishing the restored tooth.

8. The method of claim 7, wherein finishing comprises at least one of shaping and contouring the restoration.

9. The method of claim 1, wherein the enamel value restorative material includes a polymerizable resin, filler, and catalyst.

10. The method of claim 1, wherein the dentin restorative material includes a polymerizable resin, filler, and catalyst.

11. A method for fabricating a direct dental restoration having the color of a natural tooth, comprising:
   cleaning the tooth and matching the value shade of the tooth to be restored to an enamel value restorative material;
   preparing the tooth for restoration by at least one of removing decayed/damaged enamel and dentin and reshaping the tooth for cosmetic restoration;
   matching the color shade of a dentin layer of the tooth to a shaded dentin restorative material;
   applying a bonding agent to the prepared area;
   applying a flowable composite prior to applying the colored dentin material, in order to fill in any voids or irregularities that may exist in the floor of the restoration area;
   applying the matched dentin restorative material to the tooth to be restored;
   applying, over the dentin restorative material, the matched enamel value restorative material to the tooth to be restored;
   applying special effects, including staining or tinting materials or white or blue shade to the restoration prior to the final restorative layer;
   applying a translucent material to the external surface of the restoration;
   finishing by shaping or contouring the restoration; and
   polishing the restoration, wherein the color of the natural tooth is matched by the dental restoration by matching only the color shade of the dentin layer and the value shade of the enamel of the natural tooth.

* * * * *